United States Patent
Ofek et al.

(10) Patent No.: US 12,390,165 B2
(45) Date of Patent: Aug. 19, 2025

(54) CATHETER ASSEMBLY INCLUDING TRANSITIONING LUMENS

(71) Applicant: C. R. Bard, Inc., Franklin Lakes, NJ (US)

(72) Inventors: Gidon Ofek, Millcreek, UT (US); Blake Allen, South Jordan, UT (US); Todd P. McFarland, Larue, TX (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 205 days.

(21) Appl. No.: 17/405,996

(22) Filed: Aug. 18, 2021

(65) Prior Publication Data

US 2021/0378593 A1   Dec. 9, 2021

Related U.S. Application Data

(62) Division of application No. 15/469,225, filed on Mar. 24, 2017, now abandoned.

(Continued)

(51) Int. Cl.
*A61B 5/00* (2006.01)
*A61B 5/0205* (2006.01)
(Continued)

(52) U.S. Cl.
CPC ........ *A61B 5/6852* (2013.01); *A61B 5/02055* (2013.01); *A61B 5/02152* (2013.01);
(Continued)

(58) Field of Classification Search
CPC ............ A61B 5/14503; A61B 5/14532; A61B 5/14542; A61M 2025/0035;
(Continued)

(56) References Cited

U.S. PATENT DOCUMENTS 3,499,435 A * 3/1970 Rockwell ............ A61M 25/007
600/509
3,595,079 A * 7/1971 Grahn .................... A61B 5/028
73/204.22
(Continued)

FOREIGN PATENT DOCUMENTS

JP        2002065692 A  *  3/2002
WO        03/074107 A2      9/2003
WO   WO-2017165831 A1  *  9/2017   ......... A61B 5/02055

OTHER PUBLICATIONS

EP 17771276.7 filed Oct. 23, 2018 Partial European Search Report dated Sep. 25, 2019.

(Continued)

*Primary Examiner* — Nathan R Price
*Assistant Examiner* — Mark A Igel
(74) *Attorney, Agent, or Firm* — Rutan & Tucker LLP (57) ABSTRACT

A venous catheter assembly includes a hub with opposing suture wings, an extension leg coupled to the hub, and an elongate catheter tube designed for insertion into a blood vessel of a patient. The elongate catheter tube is coupled to the hub and includes at least one fluid-carrying lumen within the outer wall extending between a proximal end and a distal end of the elongate catheter tube. The fluid-carrying lumen is in fluid communication with the extension leg and an opening in the outer wall at the distal end of the elongate catheter tube. The elongate catheter tube also includes at least one terminating lumen within the outer wall extending to a closed termination point.

13 Claims, 8 Drawing Sheets

Related U.S. Application Data (60) Provisional application No. 62/313,047, filed on Mar. 24, 2016.

(51) Int. Cl.
  *A61B 5/0215* (2006.01)
  *A61B 5/145* (2006.01)
  *A61M 25/00* (2006.01)

(52) U.S. Cl.
  CPC ...... *A61B 5/14503* (2013.01); *A61B 5/14532* (2013.01); *A61B 5/14542* (2013.01); *A61M 25/0029* (2013.01); *A61M 25/0032* (2013.01); *A61M 2025/0037* (2013.01); *A61M 2025/0039* (2013.01)

(58) Field of Classification Search
  CPC .. A61M 2025/0036; A61M 2025/0039; A61M 25/0029; A61M 25/003; A61M 25/0032
  See application file for complete search history.

(56) References Cited

U.S. PATENT DOCUMENTS

| | | | | |
|---|---|---|---|---|
| 3,710,781 | A * | 1/1973 | Huthcins, IV | A61B 5/0215 600/488 |
| 3,837,347 | A * | 9/1974 | Tower | A61N 1/056 607/128 |
| 3,995,623 | A * | 12/1976 | Blake | A61B 5/287 607/125 |
| 4,329,994 | A * | 5/1982 | Cooper | A61M 25/003 604/98.01 |
| 4,878,898 | A * | 11/1989 | Griffin | A61B 5/028 604/915 |
| 4,889,128 | A * | 12/1989 | Millar | A61B 8/445 600/468 |
| 4,898,176 | A * | 2/1990 | Petre | A61B 5/0538 600/374 |
| 4,934,369 | A * | 6/1990 | Maxwell | A61B 5/6852 600/311 |
| 4,946,449 | A * | 8/1990 | Davis, Jr. | A61M 25/0075 128/DIG. 25 |
| 5,108,369 | A * | 4/1992 | Ganguly | A61B 8/12 604/523 |
| 5,366,490 | A * | 11/1994 | Edwards | A61N 5/045 607/101 |
| 5,470,308 | A * | 11/1995 | Edwards | A61B 18/1815 604/22 |
| 5,935,124 | A * | 8/1999 | Klumb | A61B 18/1492 606/45 |
| 5,971,968 | A * | 10/1999 | Tu | A61M 25/007 604/264 |
| 5,995,875 | A * | 11/1999 | Blewett | A61B 18/1477 606/41 |
| 6,036,654 | A * | 3/2000 | Quinn | A61B 5/028 604/93.01 |
| 6,183,463 | B1 * | 2/2001 | Webster, Jr. | A61B 18/1492 604/95.01 |
| 6,198,974 | B1 * | 3/2001 | Webster, Jr. | A61M 25/0136 604/95.04 |
| 6,729,334 | B1 * | 5/2004 | Baran | A61M 16/0463 128/207.14 |
| 7,998,123 | B2 * | 8/2011 | Avitsian | A61M 25/0032 604/523 |
| 8,366,698 | B2 * | 2/2013 | Avitsian | A61B 5/14503 604/523 |
| 9,033,954 | B2 * | 5/2015 | Avitsian | A61B 5/14503 604/523 |
| 2006/0253088 | A1 * | 11/2006 | Chow | A61M 25/003 604/284 |
| 2006/0258978 | A1 * | 11/2006 | Vanney | A61M 25/0041 600/152 |
| 2007/0129717 | A1 * | 6/2007 | Brown, III | A61B 18/1492 606/41 |
| 2008/0021417 | A1 * | 1/2008 | Zawacki | A61M 25/0026 604/284 |
| 2009/0240122 | A1 * | 9/2009 | Avitsian | A61M 25/0023 604/523 |
| 2011/0046457 | A1 * | 2/2011 | Gottlieb | A61M 25/0032 29/428 |
| 2012/0209221 | A1 * | 8/2012 | Patterson | A61M 25/0021 604/523 |
| 2013/0006078 | A1 * | 1/2013 | Avitsian | A61B 5/026 600/339 |
| 2013/0150688 | A1 * | 6/2013 | Avitsian | A61B 5/0205 600/325 |
| 2014/0276660 | A1 * | 9/2014 | Eckermann | A61B 5/1459 604/543 |
| 2015/0094670 | A1 * | 4/2015 | Sansoucy | B29C 65/02 29/428 |
| 2017/0273628 | A1 | 9/2017 | Ofek et al. | |

OTHER PUBLICATIONS

U.S. Appl. No. 15/469,225, filed Mar. 24, 2017 Advisory Action dated Feb. 10, 2020.
U.S. Appl. No. 15/469,225, filed Mar. 24, 2017 Final Office Action dated Nov. 22, 2019.
U.S. Appl. No. 15/469,225, filed Mar. 24, 2017 Non-Final Office Action dated Apr. 2, 2019.
U.S. Appl. No. 15/469,225, filed Mar. 24, 2017 Restriction Requirement dated Dec. 20, 2018.
U.S. Appl. No. 15/469,225, filed Mar. 3, 2017 Non-Final Office Action dated Mar. 19, 2020.
U.S. Appl. No. 15/469,225, filed Mar. 3, 2017 Non-Final Office Action dated May 18, 2021.
PCT/US17/24116 filed Mar. 24, 2017 International Search Report and Written Opinion dated Aug. 28, 2017.

* cited by examiner

CATHETER ASSEMBLY INCLUDING TRANSITIONING LUMENS

PRIORITY

This application is a division of U.S. patent application Ser. No. 15/469,225, filed Mar. 24, 2017, which claims the benefit of U.S. Provisional Application No. 62/313,047, filed Mar. 24, 2016, each of which is incorporated herein by reference in its entirety.

BRIEF SUMMARY

Briefly summarized, embodiments of the present invention are directed to a catheter assembly that includes one or more sensors that can detect and/or monitor various functions, characteristics, and/or vital measurements of a body of a patient in which the catheter assembly is placed. The sensors are placed in various positions in, on, or associated with the catheter assembly. For instance, one or more sensors can be placed so as to be in communication with one or more lumens defined by a catheter tube of the catheter assembly so as to be in contact with fluids present in the lumen(s). Yet other sensors are configured to be in proximity to the patient body but not in fluid communication therewith. Other locations are also possible and contemplated.

In one embodiment, the number of lumens defined by the catheter tube can vary as a function of longitudinal length along the catheter tube. For instance, the catheter tube can define three lumens from the proximal end of the catheter tube and terminate one of the lumens at an intermediate termination point such that only two lumens are defined further distally along the catheter tube. The terminating lumen in this case can merge with one of the other two lumens, or can simply end at a predetermined longitudinal length along the catheter tube. A sensor can be placed in the terminating lumen so as to isolate it from the other lumens and from blood or other body fluids while still enabling the sensor to reside within the patient body when the catheter tube is positioned in the patient for use. In addition to this and as will be shown further below, various other lumen transition and sensor configurations are possible.

In one embodiment, therefore, a catheter assembly is disclosed, comprising an elongate catheter tube defining at least one fluid-carrying lumen extending between a proximal end and a distal end of the catheter tube. The catheter tube further defines at least one terminating lumen defined by the catheter tube. The terminating lumen distally extends to a closed distal termination point positioned intermediately between the proximal and distal ends of the catheter tube. The termination point is defined by the catheter tube material. The terminating lumen is configured to be isolated from fluids.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a catheter assembly that includes one or more sensors that can detect and/or monitor various functions, characteristics, and/or vital measurements of a body of a patient in which the catheter assembly is placed. The sensors are placed in various positions in, on, or associated with the catheter assembly. For instance, one or more sensors can be placed so as to be in communication with one or more lumens defined by a catheter tube of the catheter assembly so as to be in contact with fluids present in the lumen(s). Yet other sensors are configured to be in proximity to the patient body but not in fluid communication therewith. Other locations are also possible and contemplated.

In accordance with one embodiment, the number of lumens defined by the catheter tube can vary as a function of longitudinal length along the catheter tube. For instance, the catheter tube can define three lumens from the proximal end of the catheter tube and terminate one of the lumens at an intermediate termination point such that only two lumens are defined further distally along the catheter tube. The terminating lumen in this case can merge with one of the other two lumens, or can simply end at a predetermined longitudinal length along the catheter tube. A sensor can be placed in the terminating lumen so as to isolate it from the other lumens and from blood or other body fluids while still enabling the sensor to reside within the patient body when the catheter tube is positioned in the patient for use. In addition to this and as will be shown further below, various other lumen transition configurations are possible.

In yet another embodiment, various catheter tube lumen configurations are disclosed that enable a sensor to be placed proximate the distal end of the catheter tube, with an accompanying sensor wire(s) extending from the proximal end of the catheter tube to the distally-disposed sensor so as to provide for functionality of the sensor. The sensor wires can be provided a pathway via a dedicated sensor wire lumen, or by incorporation into the catheter tube wall of septum, in one embodiment. These pathways are provided in addition to one or more functional infusion/aspiration lumens also defined by the catheter tube. Placement of the sensor in this manner enables the sensor to be located within the patient body and proximate a desired location while still being included as part of the catheter assembly.

Figure 1:
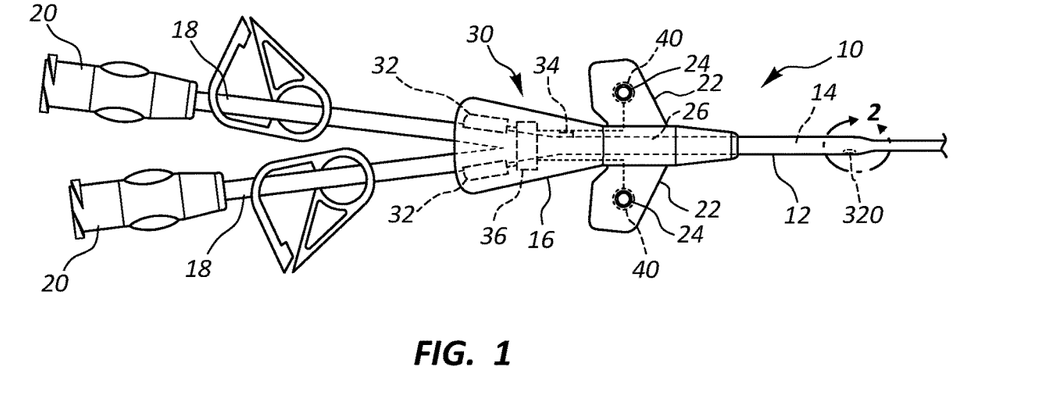
FIG. 1 is a side view of a catheter assembly including a plurality of sensors in accordance with one embodiment.

Reference is first made to FIG. 1, which depicts various details of a catheter assembly ("catheter"), generally designated at 10, in accordance with one embodiment. As shown, the catheter 10 includes an elongate catheter tube 12 defining one or more lumens 14 extending between a proximal end 12A and a distal end 12B thereof. The proximal end 12A of the catheter tube is operably connected to a bifurcation hub ("hub") 16, which in turn is operably connected to one or more extension legs 18. A connector 20, such as a Luer connector, is disposed on a proximal end of the extension leg 18. The hub 16 includes two suture wings 22 that oppositely extend from the body of the hub 16. Each suture wing 22 includes a suture hole 24. Note that the hub 16 is also referred to herein as a "bifurcation hub" even in cases where only one fluid passageway is defined therethrough.

In accordance with one embodiment, one or more sensors, also referred to herein as a "sensor array" 30, are included with the catheter 10 to enable the detection of data relating to one or more physiological aspects of the patient and/or physical aspects of the catheter when the catheter tube 12 is disposed in the vasculature (as discussed here) or other suitable internal portion of the body of the patient. In the present embodiment, multiple sensors are included with the catheter 10, though the number, type, size, placement, function, and desired uses of the various sensors can vary from what is shown and described herein. Note that the sensor array 30 can, in one embodiment, include only one sensor. Note also that, where only one of a particular sensor is discussed below, it is appreciated that more than one of a particular type of sensor can be included, in the same or different locations within the catheter assembly.

As shown in FIG. 1, a pressure sensor 32 is included as part of the sensor array 30. In the present embodiment, the pressure sensor 32 includes a central venous pressure ("CVP") sensor and is disposed so as enable venous pressure of the patient to be sensed via the fluid (such as blood and/or saline) typically present within the lumen 14 of the catheter tube 12. As shown, in the present embodiment the pressure sensor 32 is disposed within the hub 16 so as to be in operable communication with a fluid passageway 26 within the hub that is in turn in fluid communication with the lumen 14 of the single-lumen catheter tube 12 shown in FIG. 1. Other pressure sensor locations can also employed, including within the catheter tube 12, the extension leg 18, etc. In one embodiment, the pressure sensor 32 is a medical pressure sensor NPC-100 or NPC-120, manufactured by Amphenol Corporation, though other pressure sensors may also be employed. In another embodiment, the pressure sensor includes a strain-sensitive Wheatstone bridge. The sensing surface of the pressure sensor 32 in the present embodiment is in direct contact with fluid present in the fluid passageway of the hub 16. Note that the size, shape, and other configuration of the hub 16 may be increased from what is shown and described herein in order to accommodate the sensor array 30, in one embodiment.

An ECG sensor 34, also referred to herein as an ECG electrode or electrical sensor, is also included with the catheter assembly to enable ECG signals emanating from the heart of the patient to be detected, in conjunction with an additional ECG sensor/electrode located on the patient's skin or external portion of the catheter assembly/proximate the catheter assembly, in one embodiment. As shown, in the present embodiment the ECG sensor 34 is also disposed within the hub 16 so as to be in direct contact with fluid present in the hub fluid passageway 26 and the lumen 14 of the catheter tube 12. Other ECG sensor locations can also be employed, including within the catheter tube 12, the extension leg 18, etc. In the present embodiment, the ECG sensor 34 includes a conductive wire that is able to detect ECG signals of the patient heart that are present in the fluid of the hub fluid passageway 26 and catheter tube lumen 14, though other types of ECG sensors can be employed. Further details regarding a system and method for using an ECG sensor for guiding the catheter assembly to a desired position within the body of a patient can be found in U.S. Pat. No. 8,849,382, entitled "Apparatus and Display Methods Relating to Intravascular Placement of a Catheter," which is incorporated herein by reference in its entirety.

As described, the sensor array 30—including here the pressure sensor 32 and the ECG sensor 34—is disposed within the hub 16, which is sized to provide the needed volume for such sensors. Note that the size, shape, and configuration of the hub 16 can vary from what is shown and described in order to house the sensor(s). In other embodiments, the sensors can be located in other portions of the catheter 10, including along or at either end of the catheter tube 12, the extension leg(s) 18, etc. Also note that a variety of sensors for detecting body measurements, physiological aspects of the patient, and/or physical aspects of the catheter can be included with the catheter assembly, some of which are discussed further below.

FIG. 1 further shows that the hub 16 (or other suitable location) includes a printed circuit board ("PCB") 36 that is configured to govern operation of the sensor array 30, here including the pressure sensor 32 and the ECG sensor 34. In one embodiment, the PCB 36 includes a microprocessor for governing sensor operation. In one embodiment, the PCB 36 can further include a power source for powering the sensor array 30, though in other embodiments the power source can be remotely disposed from the PCB, and even the catheter 10. A non-volatile memory storage location, such as flash memory for instance, can also be included on the PCB 36 to enable data sensed by the sensors of the sensor array 30 to be temporarily or permanently stored thereon. The storage location can be accessible by a user or can be transmitted to a desired location in a suitable manner.

In the present embodiment, the PCB 36 further includes a transmission module, such as a radio for enabling the PCB to transmit sensor data wirelessly to another receipt location, such as those referred to further above. Such wireless transmission can occur via Bluetooth, Wi-Fi, rF, near-field communication ("NFC"), GPS, ANT, ZigBee, or other manner utilizing electromagnetic radiation. In another embodiment, the sensor data can be transmitted from the catheter 10 via a physical connection, such as via a removable physical connection, wires, etc. In another embodiment and as mentioned, sensor data, e.g., central venous pressure, ECG signals, temperature, etc., are stored in a memory location included on the PCB 36, or other location on the catheter 10. In yet another embodiment, the PCB 36 includes a clock/timer circuit.

In the present embodiment of FIG. 1, the suture holes 24 of the suture wings 22 are configured to include electrical contacts to provide power to the sensors 32 and 34 of the sensor array 30, as well as to the PCB 36. In particular, an annular electrical contact 40 is included in each suture hole 24 of the bifurcation hub suture wings 22, with the electrical contacts being operably connected to the PCB 36 and sensor array 30. A securement device is configured to be placed on the skin of the patient and operably connect with and secure in place the catheter 10 once the distal portion of the catheter has been inserted into the patient. To that end, the securement device in one embodiment includes a retainer mounted to an adhesive pad, and securement arms that are hinged so as to removably pivot atop the suture wings 22 of the bifurcation hub 16 (in a snap-fit arrangement) to secure the bifurcation hub in place.

In one embodiment, the securement device 50 includes additional functionality to provide power to the sensor array 30 and PCB 36. In detail, the securement device can include two posts, each of which is configured to serve as an electrical contact and each of which is operably connected with a battery, also included in the securement device. The posts are configured to be received within the corresponding suture holes 24 of the catheter suture wings 22 such that electrical contact is established with the electrical contacts 40 of the suture holes. The battery included on the securement device can, in this way, provide electrical power to the sensors 32, 34 and the PCB 36 of the catheter hub 16. Of course, other external power sources can be employed. In one embodiment, electrical contacts between the catheter and the securement device can also be utilized to transfer sensor data therebetween. In another embodiment, the securement device can include a radio or other mode for transmitting sensor data received from the catheter. In yet another embodiment, the PCB or a sensor can be included on the securement device. It is appreciated that the size, shape, and other configuration of the securement device can vary from what is shown and described herein. Further details regarding the catheter assembly 10 with one or more included sensors can be found in U.S. Pat. No. 10,433,790, filed Sep. 23, 2016, and entitled "Catheter Assembly Including Monitoring Capabilities," which is incorporated herein by reference in its entirety. Note that the principles discussed in the present disclosure can be employed in catheters and elongate tubular devices that include no sensor, or one or more sensors as may be appreciated.

Though shown in FIG. 1 as a dual lumen catheter assembly in the configuration of a PICC, it should be appreciated that this is but one example of a catheter that can benefit from the teachings herein. Indeed, catheters and elongate tubular devices of various types can employ the teachings disclosed herein, including PICCs, CVCs, dialysis catheters, Foley and urinary catheters, feeding tubes, arterial catheters, balloon catheters, PIVs, etc.

Figure 2:
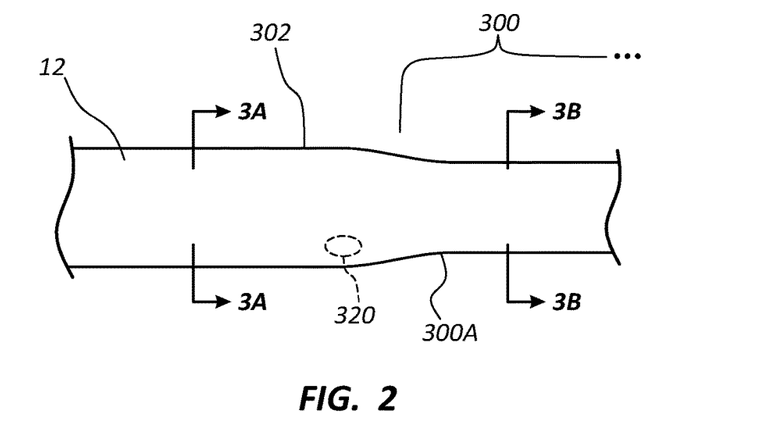
FIG. 2 is a side view of a catheter tube according to one embodiment.
Figure 3A:
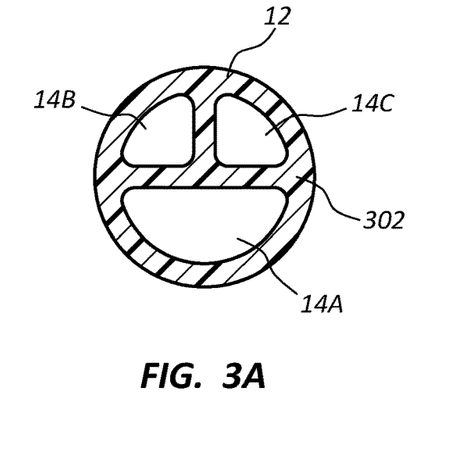
FIGS. 3A-3C depict various views of the catheter tube of FIG. 2.

Together with FIG. 1, reference is now made to FIGS. 2 and 3A-3C. In detail, FIG. 2 depicts a portion of the catheter tube 12 of the catheter assembly 10 of FIG. 1, wherein the catheter tube includes a reduced-diameter portion 300, wherein the outer diameter of the catheter tube 12 is reduced relative a more proximal un-reduced portion of the catheter tube. In accordance with one embodiment, the number of lumens 14 defined by the catheter tube 12 varies along the longitudinal length of the catheter tube. As seen in FIG. 3A, which shows a cross-sectional view of the catheter tube 12 taken along section A-A (FIG. 2), the catheter tube defines three lumens 14A, 14B, and 14C in a proximal portion of the catheter tube, such as the portion extending distally from the hub 16 to a proximal end 300A of the reduced diameter portion 300.

Figure 3B:
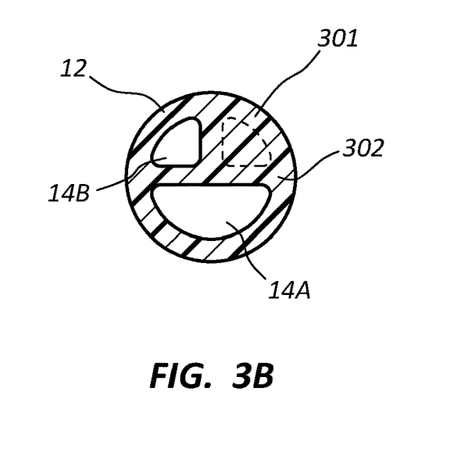

FIG. 3B shows that substantially at the proximal end 300A of the reduced diameter portion 300, lumen 14C is closed and the area formerly occupied by the lumen becomes part of a catheter tube wall 302, indicated by a tube wall region 301 in FIG. 3B. Indeed FIG. 3B, which is a cross-sectional view of the catheter tube 12 of FIG. 2 taken along section B-B, shows only the two remaining lumens 14A and 14B. In the present embodiment, the loss of the lumen 14C accounts for the reduced outer diameter size of the catheter tube 12 in the reduced diameter portion 300 as the triple lumen catheter tube transitions to only a dual-lumen catheter tube. The reduced diameter portion 300 in the present embodiment extends the remaining distal length of the catheter tube 12, though this may vary in other embodiments. Reduction of the outer diameter of the catheter tube 12 in the reduced diameter portion 300 results in less occlusion of the vein or other vessel in which the catheter tube is disposed, which in turn can reduce the incidence of deep vein thrombosis and other catheter-related complications. In other embodiments, however, no reduction of the catheter tube size is necessary.

Figure 3C:
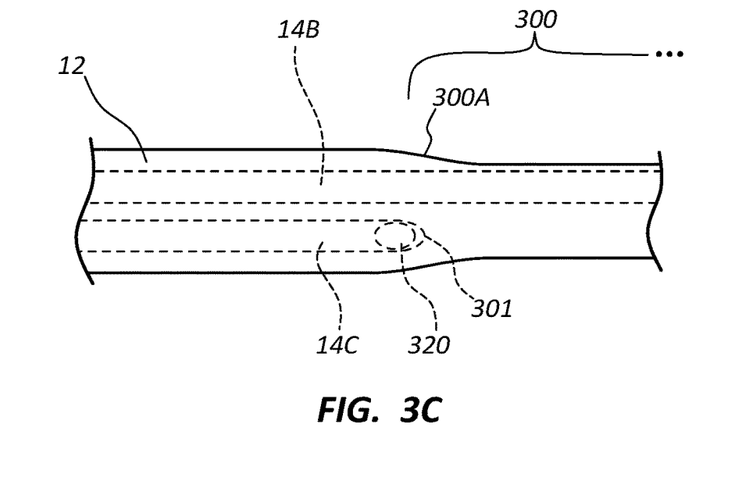

It is thus appreciated that the lumen 14C is considered a terminating lumen as it extends from the proximal end 12A of the catheter tube 12 to the proximal end 300A of the reduced diameter portion 300, where it terminates at a closed, distal termination point, as seen in FIG. 3C. So configured, the distal termination point of the lumen 14C provides a location for the placement of a sensor 320 (FIG. 1, 3C) in the lumen, where it can be secured and be protected from removal from the catheter tube 12. Though in the present embodiment the lumen 14C remains separate from the other lumens 14A and 14B, the lumen 14C upon termination can combine with another lumen or lumens in other embodiments.

As mentioned, the sensor 320 is placed in a distal portion of the terminating lumen 14C, as seen in FIGS. 1 and 3C, though other placements within the terminating lumen 14C are also possible. The sensor 320 in the present embodiment is a temperature sensor for measuring an internal body temperature of the patient when the catheter assembly 10 is disposed within the body of the patient. The sensor 320 here is representative of a variety of types of sensors and electronic or medical components that can be placed in the terminating lumen to acquire data relating to the patient or to assist in patient care. As such, the disclosure herein is not intended to be limiting.

It is appreciated that in the present embodiment the terminating lumen 14C is isolated from fluids transported through the catheter tube 12 such that the sensor 320 is not in contact with such fluids. In other embodiments, however, fluids could be inserted into the lumen if desired, recognizing that no outlet exists for such fluids other than at the proximal portion of the catheter tube. Or a skive cut or other hole could be defined near the distal end of the terminating lumen in one embodiment to enable direct contact of the sensor with blood of the patient.

In yet another embodiment, the terminating lumen 14C could be extended in length and open near the distal end 12B of the catheter tube 12, extend proximally as a lumen, and terminate at a relatively more proximal portion of the catheter tube, effectively reversing the configuration shown in FIG. 3C, either with or without the reduced diameter portion of the catheter tube. In yet another embodiment, a first terminating lumen can extend distally from the proximal end of the catheter tube, while another terminating lumen extends proximally from or near the distal end of the catheter tube. These and other configurations are contemplated.

Note that one or more of a variety of sensors can be included in the terminating lumen, including light-based sensors, glucose meters, blood oxygen sensors, SvO2 sensors, temperature sensors, pressure sensors, CVP sensors, lactic acid sensor, thermistors, etc. Note further that use of a terminating lumen as described herein obviates the use of potting to plug an otherwise patent lumen so a sensor could be placed therein. As such, the potential dislodgement of potting from the catheter tube lumen and entry into the vessel is avoided.

Note that the catheter assembly 10 of FIG. 1 includes the three lumens 14A, 14B, and 14C extending distally from the proximal end thereof, but only two extension legs 18. In the present embodiment, the lumens that extend the length of the catheter tube 12, i.e., lumens 14A and 14B are correspondingly operably connected to the extension legs 18, while the terminating lumen 14C includes an access port at the bifurcation hub 16, but no extension leg. In other embodiments, the terminating lumen 14C can share an extension with one of the other lumens, or can be sealed so as to include no access port, in one embodiment. These and other modifications are contemplated.

It is appreciated that the catheter tube 12 and its lumen configuration as described above in connection with FIGS. 2-3C can be manufactured in one or more ways, though in one embodiment the lumen 14C is terminated during an extrusion process. Briefly, an extrusion material is extruded through a properly configured die to form a continuous length of catheter tubing. Pins are positioned in the extrusion pathway to define the various lumens of the catheter tubing, such as the lumens 14A, 14B, and 14C of the catheter assembly 10 shown in FIG. 1, for example. The terminating lumen 14C is formed by removing the corresponding pin that defines the terminating lumen at the desired point during extrusion of the catheter tubing, while keeping the other pins for defining the lumens 14A and 14B in place. The pressure of injection air blown through the pins to keep the lumens inflated during the extrusion process, together with a pull rate of the catheter tubing as it is pulled from the extrusion machine, can be modified to maintain the catheter tubing and lumen configuration as desired. Once it has sufficiently cured, the catheter tubing is cut into appropriate lengths to form the catheter tube, such as the catheter tube 12 shown in FIG. 1, with the terminating lumen 14C present as has been described above. In another embodiment, no pin is removed; instead, the pull rate and/or injection air pressure are regulated so as to terminate one or more of the lumens along the longitudinal length of the catheter tubing. Generally, it is appreciated that the catheter tube 12 can include more than one terminating lumen, with each of the lumens terminating at different termination points along the length of the catheter tube.

Figure 4:
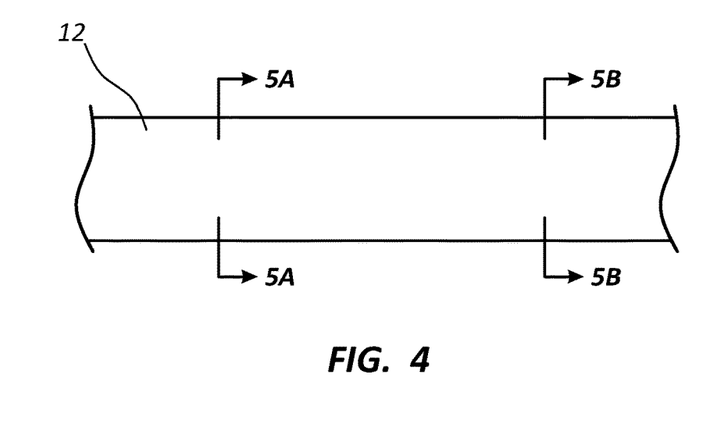
FIG. 4 is a side view of a catheter tube according to one embodiment.
Figure 5A:
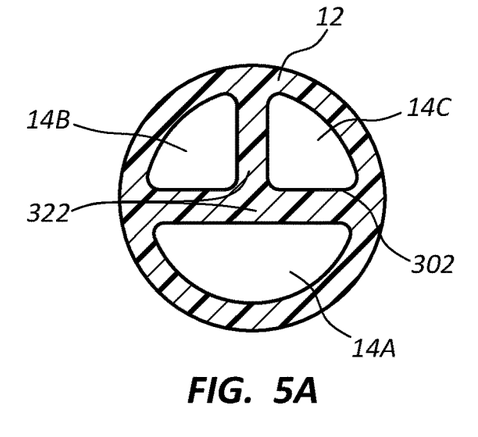
FIGS. 5A and 5B show cross-sectional views of the catheter tube of FIG. 4 according to one embodiment.
Figure 5B:
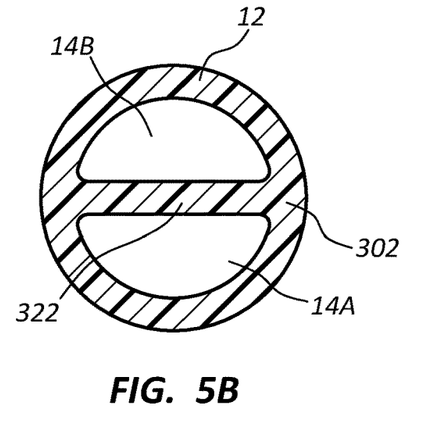

FIGS. 4, 5A, and 5B depict details of a portion of the catheter tube 12 according to another embodiment, wherein the outer diameter of the catheter tube does not vary in diameter along its longitudinal length, in contrast to the catheter tube shown in FIG. 2. As shown by the cross-sectional view of the catheter tube 12 in FIG. 5A, which is taken along the section A-A in FIG. 4, a relatively proximal portion of the catheter tube defines three lumens 14A, 14B, and 14C. In contrast, a relatively more distal portion of the catheter tube 12, as shown by FIG. 5B, which is taken along the section B-B in FIG. 4, defines only lumens 14A and 14B, with the third lumen 14C having been terminated at a distal termination point proximal to this cross section, thus becoming a terminating lumen.

Correspondingly, the lumen 14B as shown in FIG. 5B has increased in size to occupy the cross-sectional space formerly occupied by the lumen 14C. Thus, it is shown that not only can the number of lumens vary along the longitudinal length of the catheter tube, but the relative sizes of the lumens can vary as well. As before, it is appreciated that the lumen 14C terminates at a predetermined distal termination point along the longitudinal length of the catheter tube 12 at a predetermined distance distally from the proximal end 12A of the catheter tube. Such a termination point of the terminating lumen 14C provides a suitable location for the placement of a sensor, or for other purposes that may be appreciated. The sensor may be placed in a relatively proximal location within the terminating lumen so as to reside more peripherally (such as in the patient's arm) when the catheter tube is disposed within the patient body, or more distally (such as proximate the patient's heart).

Figure 6A:
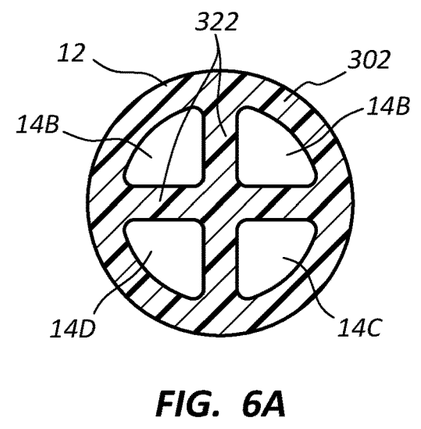
FIGS. 6A and 6B show cross-sectional views of the catheter tube of FIG. 4 according to one embodiment.
Figure 6B:
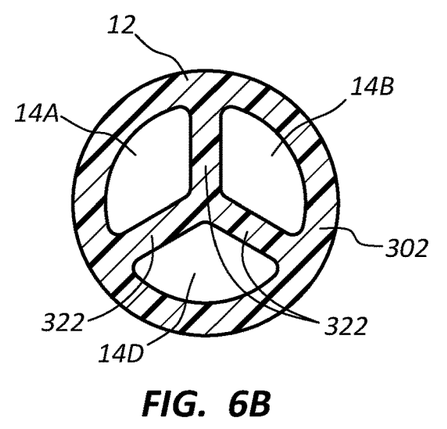

FIGS. 6A and 6B show another catheter tube lumen transition configuration according to one embodiment, wherein a proximal portion of the catheter tube 12 includes a quad lumen configuration including lumens 14A, 14B, 14C, and 14D, as shown in FIG. 6A. The third lumen 14C is a terminating lumen and terminates at a distal termination point of the catheter tube 12 proximal to the cross section shown in FIG. 6B, in the manner described above to transition the catheter tube to a triple lumen catheter tube including only lumens 14A, 14B, and 14D. Correspondingly, the sizes of the lumens 14A, 14B, and 14D are larger relative their more proximal portions, made possible by the termination of the third lumen 14C. It is appreciated that any one or more of the lumens can be terminated at any one of a variety of termination points along the longitudinal length of the catheter tube 12 to produce a transitioning lumen catheter tube of a variety of configurations. In another embodiment, it is appreciated that one or more lumens can be added at a relatively more distal point to a catheter tube including fewer lumens in the proximal portion of the catheter tube. These and other modifications are contemplated.

Figure 7A:
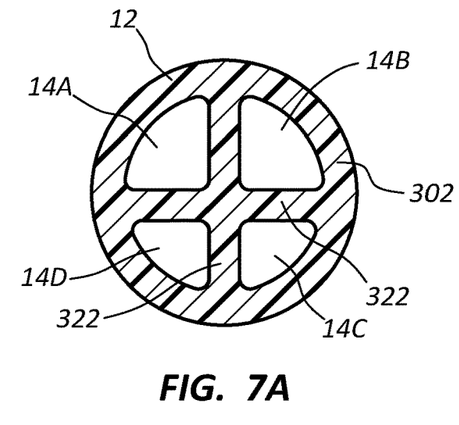
FIGS. 7A and 7B show cross-sectional views of the catheter tube of FIG. 4 according to one embodiment.
Figure 7B:
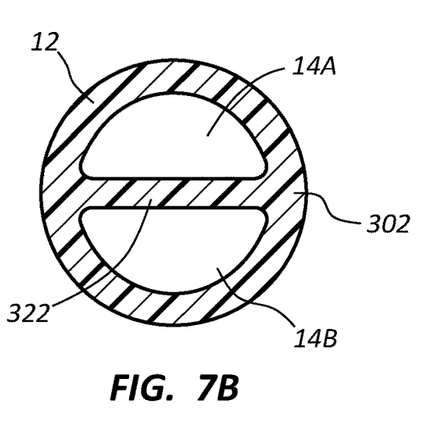

FIGS. 7A and 7B show another catheter tube lumen transition configuration according to one embodiment, wherein a proximal portion of the catheter tube 12 includes a quad lumen configuration including lumens 14A, 14B, 14C, and 14D, as shown in FIG. 7A. The second lumen 14B and the third lumen 14C terminate at a more distal portion of the catheter tube 12, as shown in FIG. 7B, in the manner described above to transition the catheter tube to a dual lumen catheter tube including only lumens 14A and 14D. Correspondingly, the sizes of the lumens 14A and 14D are larger relative their more proximal portions, made possible by the termination of the second and third lumens 14B, 14C.

Figure 8:
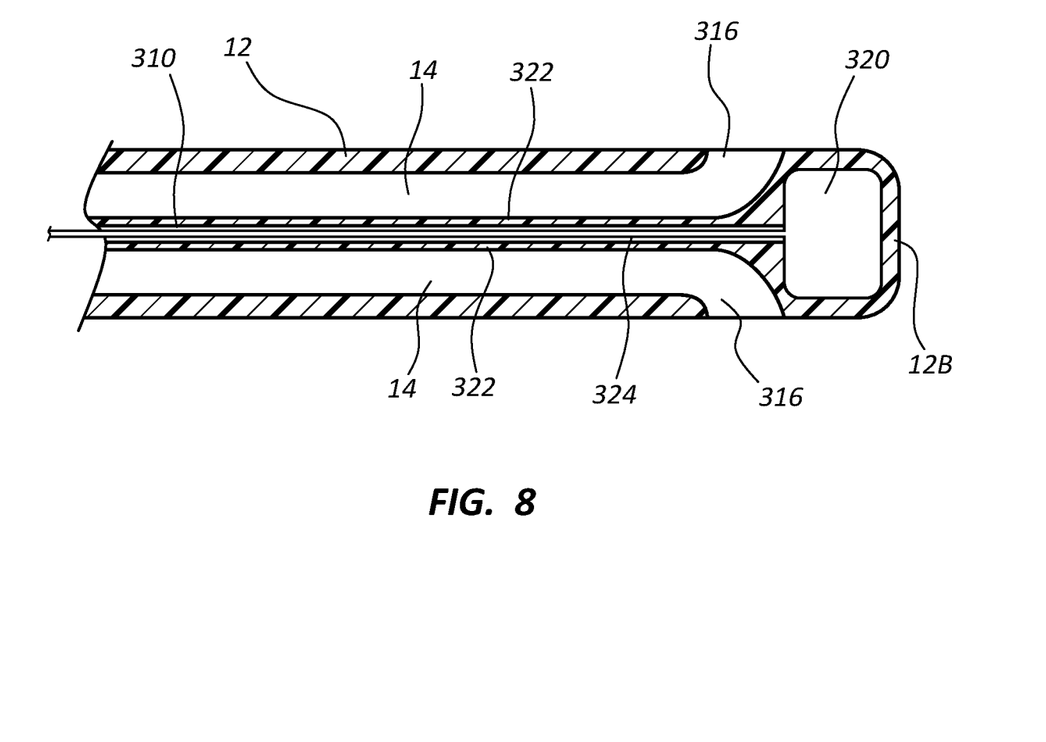
FIG. 8 is a cross sectional side view of a catheter tube including a distally-located sensor according to one embodiment.

Reference is now made to FIG. 8, which depicts the catheter tube 12 according to one embodiment. As shown, the catheter tube 12 includes two fluid-carrying lumens 14 for infusion and/or aspiration of fluids therethrough that are defined to extend substantially the longitudinal length of the catheter tube. Corresponding side outlets 316 are disposed through the catheter tube wall, as shown.

A sensor 320, such as those described further above, is disposed in a distal portion of the catheter tube 12 near a distal end 12B there. In the present embodiment, the sensor 320 is disposed in a pocket and is isolated from the lumens 14 so as to not be in fluid communication therewith, though in other embodiments it is appreciated that the sensor can be placed in fluid communication with one or more fluid-carrying lumens.

A sensor lumen 310 is also included and extends substantially the length of the catheter tube 12 so as to provide a route along which a sensor wire 324 can extend through the catheter tube to the sensor 320 disposed near the distal end 12B thereof. This enables the sensor 320 to be electrical powered and/or to provide a route by which data and/or measurements can be transmitted to outside the patient body. Note that the sensor wire 324 can extend past the proximal end 12A of the catheter tube 12 and include an appropriate connector to enable it to operably connect to a data measurement device or other suitable component, as may be appreciated.

Note that the catheter tube 12 including the distally placed sensor 320 shown in FIG. 8, can be formed in one embodiment by first extruding the catheter tube, then placing the sensor 320 and sensor wire 324 in place. The distal end is then tipped, such as by rF tipping, to form the closed distal end. In another embodiment, the closed distal end about the sensor 320 is formed by adding uncured silicone to the distal portion of an extruded silicone catheter tube 12, shaping the distal end as needed (such as via a form, cup, or mold), then curing the silicone tip. In yet another embodiment, the distal portion of the catheter tube 12, including the sensor 320, can first be formed, then joined to the open distal end of the catheter tube 12 via solvent bonding, epoxy, or other suitable adhesive. These techniques can also be applied to the other embodiments discussed herein.

Figure 12:
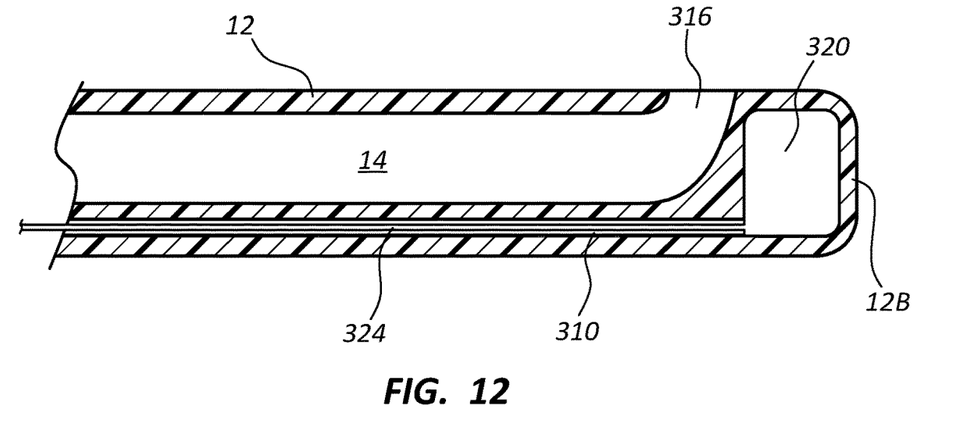
FIG. 12 is a cross sectional side view of a catheter tube including a distally-located sensor according to one embodiment.
Figure 13:
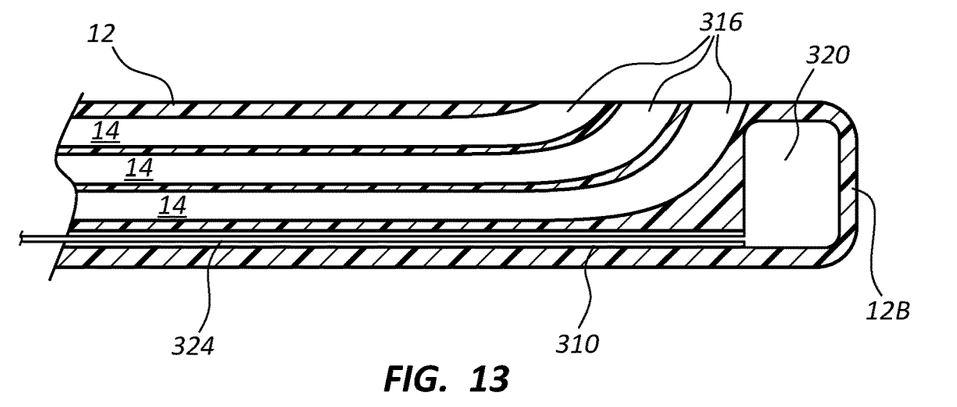
FIG. 13 is a cross sectional side view of a catheter tube including a distally-located sensor according to one embodiment.
Figure 14:
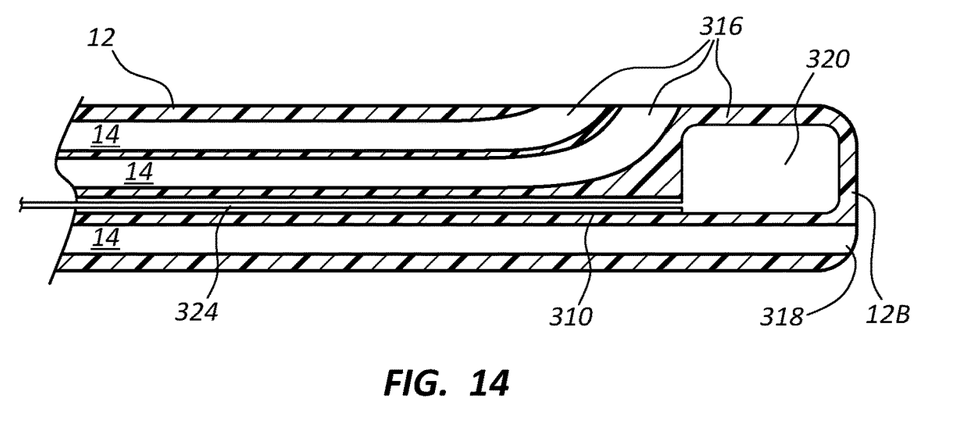
FIG. 14 is a cross sectional side view of a catheter tube including a distally-located sensor according to one embodiment.

Variations to the configuration of the catheter tube 12 as depicted in FIG. 8 are also contemplated. FIG. 12 gives an example of this, wherein only a single fluid-carrying lumen 14 is included, together with the sensor lumen 310, which is in on offset position. FIG. 13 shows the catheter tube 12 as including three fluid-carrying lumens 14 with the offset sensor lumen 310. And FIG. 14 shows the catheter tube 12 as including two fluid-carrying lumens 14 that exit to side openings 316, a single fluid-carrying lumen 14 that exits at a distal end opening 318, and the sensor lumen 310 interposed therebetween. Note that any one or more of the side openings 316/distal end opening 318 can include valved openings, in one embodiment. Also the lumens 14 can be configured so as to exit at side openings 316 (or other openings) at various distances along the length of the catheter tube. These and other configurations are therefore appreciated as comprising part of the present disclosure.

Figure 9:
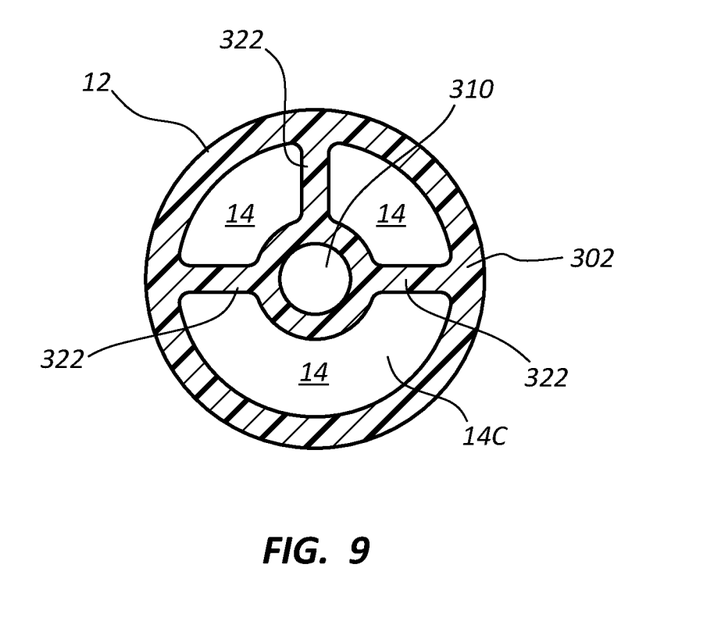
FIG. 9 is a cross-sectional view of a catheter tube with an included sensor lumen in accordance with one embodiment.

FIG. 9 shows a cross-sectional view of the catheter tube 12 according to one embodiment, wherein three fluid-carrying lumens 14 are shown as defined by a catheter tube wall 302 and septa 322, together with a centrally disposed sensor lumen 310. The sensor lumen 310 can be used as a conduit through which one or more wires can be extended to operably connect a sensor disposed in a distal (or other) portion of the catheter tube, such as the sensor 320 of FIG. 8, for instance.

Figure 10:
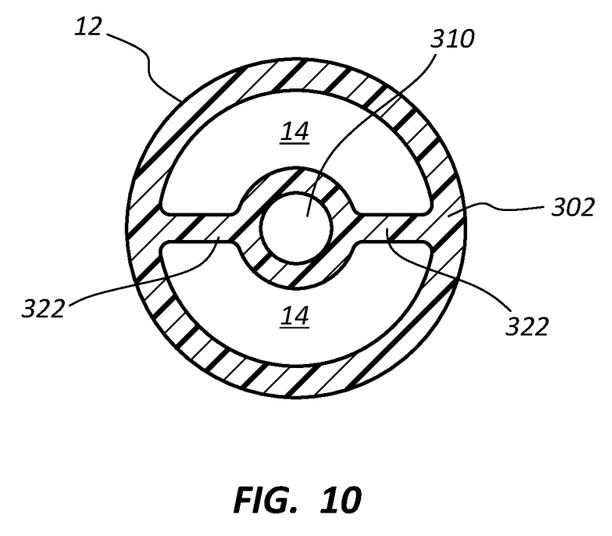
FIG. 10 is a cross-sectional view of a catheter tube with an included sensor lumen in accordance with one embodiment.
Figure 11:
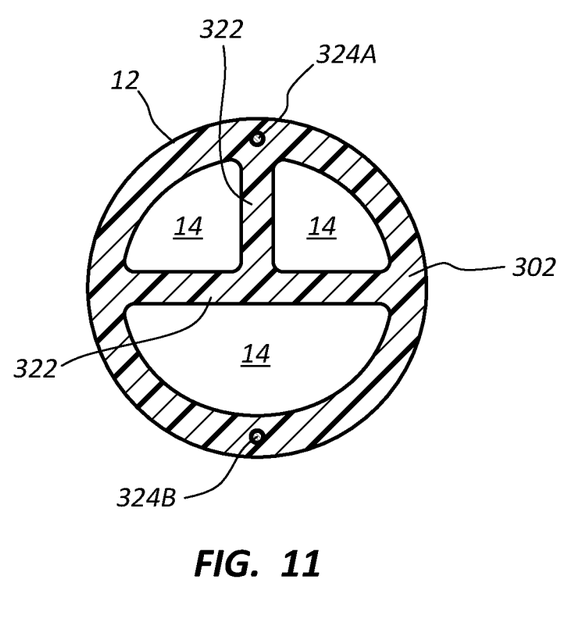
FIG. 11 is a cross-sectional view of a catheter tube with an included sensor wire configuration in accordance with one embodiment.
Figure 18:
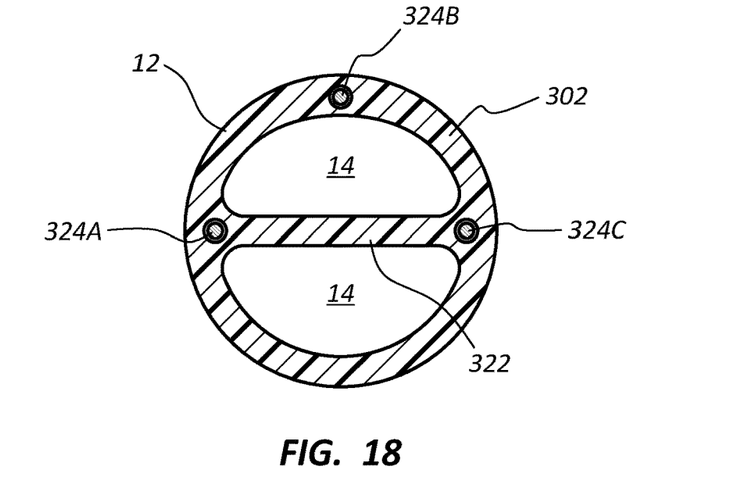
FIG. 18 is a cross-sectional view of a catheter tube with an included sensor wire configuration in accordance with one embodiment.
Figure 19:
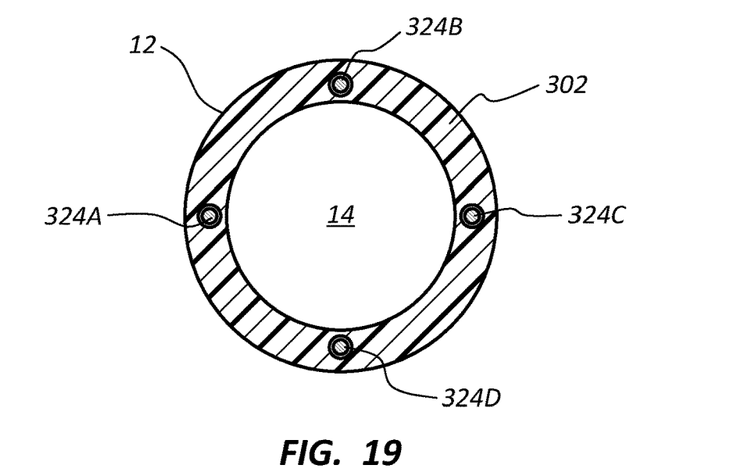
FIG. 19 is a cross-sectional view of a catheter tube with an included sensor wire configuration in accordance with one embodiment.

The size, shape, location, and other configuration of the sensor lumen 310 can vary from that shown in FIG. 9. Indeed, FIG. 10 depicts another possible cross-sectional lumen configuration, wherein two fluid-carrying lumens 14 are included with a centrally disposed sensor lumen 310. FIG. 11 depicts the catheter tube 12 including three fluid-carrying lumens 14 and two sensor wires 324A, 324B disposed in and integrated with the catheter tube wall 302 such that no sensor lumen is required, thus requiring no size sacrifice for fluid-carrying lumens. FIGS. 18 and 19 depict variations of this configuration, wherein the catheter tube 12 defines two fluid-carrying lumens 14 and three sensor wires 324A, 324B, and 324 C integrated with the catheter tube wall 302 (FIG. 18) or one fluid-carrying lumen 14 and four sensor wires 324A, 324B, 324C, and 324D.

Figure 15:
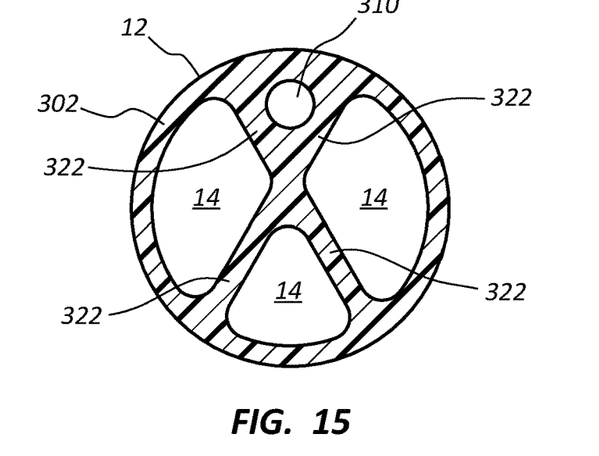
FIG. 15 is a cross-sectional view of a catheter tube with an included sensor lumen in accordance with one embodiment.
Figure 16:
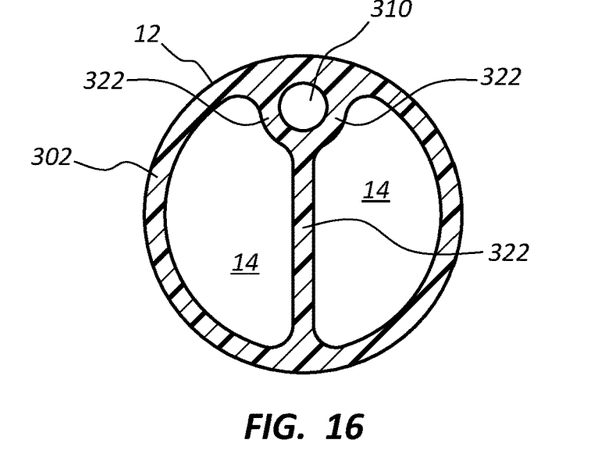
FIG. 16 is a cross-sectional view of a catheter tube with an included sensor lumen in accordance with one embodiment.
Figure 17:
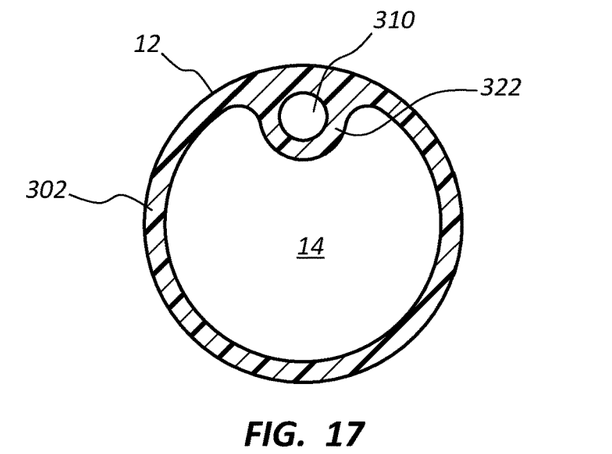
FIG. 17 is a cross-sectional view of a catheter tube with an included sensor lumen in accordance with one embodiment.

FIG. 15 depicts the catheter tube 12 including three fluid-carrying lumens 14 and an offset sensor lumen 310. FIG. 16 depicts the catheter tube 12 including two fluid-carrying lumens 14 and an offset sensor lumen 310. FIG. 17 depicts the catheter tube 12 including a single fluid-carrying lumen 14 and an offset sensor lumen 310.

It is appreciated that placement and configuration of the integrated sensor wire locations and/or sensor lumen can be implemented in a variety of ways. In one embodiment, the sensor wires can be integrated with the septum 322 instead of the catheter tube wall 302. Also, more than one sensor wire or sensor lumen can be included to operably connect one or more sensors. The wire can include one or more wires, such as in a twisted pair configuration, for example. The number of fluid-carrying lumens can also vary in size, shape, number, etc., as can the size, placement, and configuration of the sensor lumen itself. In addition, note that the size, position, and type of sensors included with the catheter tube can vary from what is shown and described, as can the outlets of the fluid-carrying lumens.

Figure 20:
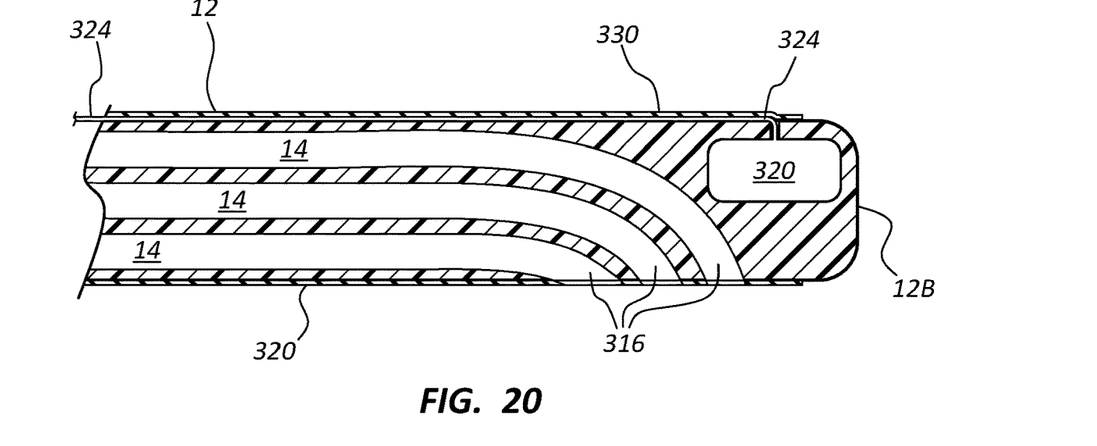
FIG. 20 is a cross-sectional view of a catheter tube with an included sensor wire configuration in accordance with one embodiment.

FIG. 20 shows the catheter tube 12 according to another embodiment, wherein three fluid-carrying lumens 14 are included, together with the sensor 320 disposed in a distal portion of the catheter tube. The sensor wire 324 extends along the length of an outer surface of the catheter tube 12 to the sensor 320. A cover material 330 is placed over the sensor wall on the other surface of the catheter tube 12. The cover material 330 can be selected of one of a variety of suitable materials, including polyurethane film, heat-shrink material, etc.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A venous catheter assembly, comprising:
    a hub including opposing suture wings;
    an extension leg coupled to the hub; and
    an elongate catheter tube designed for insertion into a blood vessel of a patient, the elongate catheter tube coupled to the hub, the elongate catheter tube defining an outer wall circumscribing a plurality of lumens, the plurality of lumens comprising:
        at least one fluid-carrying lumen within the outer wall extending between a proximal end and a distal end of the elongate catheter tube, the at least one fluid-carrying lumen in fluid communication with the extension leg and an opening in the outer wall at the distal end of the elongate catheter tube; and
        at least one terminating lumen within the outer wall extending to a closed termination point within the outer wall, the closed termination point positioned in a proximal end of a reduced diameter portion of the elongate catheter tube intermediately between the proximal end and the distal end of the elongate catheter tube, wherein a diameter of the elongate catheter tube in the reduced diameter portion of the elongate catheter tube is reduced in size distal to the closed termination point for a remaining distal length of the elongate catheter tube due to loss of the at least one terminating lumen.

2. The venous catheter assembly according to claim 1, wherein the at least one terminating lumen distally extends from the proximal end of the elongate catheter tube.

3. The venous catheter assembly according to claim 1, wherein the closed termination point is positioned in the elongate catheter tube to be disposed within the blood vessel of the patient.

4. The venous catheter assembly according to claim 1, further comprising a sensor disposed in the at least one terminating lumen proximate the closed termination point.

5. The venous catheter assembly according to claim 4, wherein the sensor is at least one of a light-based sensor, a glucose meter, a blood oxygen sensor, a temperature sensor, or a thermistor.

6. The venous catheter assembly according to claim 4, further comprising at least one wire that extends along the at least one terminating lumen configured to operably connect the sensor to an apparatus separate from the venous catheter assembly.

7. The venous catheter assembly according to claim 1, wherein the elongate catheter tube includes a plurality of fluid-carrying lumens.

8. The venous catheter assembly according to claim 7, wherein a cross-sectional size of one of the plurality of fluid-carrying lumens changes at a point distal to the closed termination point relative to a point proximal to the closed termination point.

9. The venous catheter assembly according to claim 7, wherein cross-sectional sizes of the plurality of fluid-carrying lumens remain substantially the same at a point distal to the closed termination point relative to a point proximal to the closed termination point.

10. The venous catheter assembly according to claim 1, wherein the at least one terminating lumen includes an access port on a proximal portion of the venous catheter assembly.

11. A venous catheter assembly, comprising:
    a hub including opposing suture wings;
    an extension leg coupled to the hub;
    a catheter tube designed for insertion into a blood vessel of a patient, the catheter tube coupled to the hub, the catheter tube defining a plurality of lumens, the plurality of lumens comprising:
        at least one fluid-carrying lumen extending from a proximal end to a distal end of the catheter tube, the at least one fluid-carrying lumen in fluid communication with the extension leg and a side opening at the distal end of the catheter tube; and
        a terminating lumen distally extending from a proximal portion of the catheter tube to a closed termination point positioned distal of the side opening, wherein the plurality of lumens are greater in number proximal of the closed termination point than distal of the closed termination point;
    a sensor disposed in the terminating lumen; and
    a sensor wire operably connected to the sensor.

12. The venous catheter assembly according to claim 11, wherein the sensor is at least one of a light-based sensor, a glucose meter, a blood oxygen sensor, a temperature sensor, or a thermistor.

13. The venous catheter assembly according to claim 11, wherein the catheter tube includes a plurality of fluid-carrying lumens.

* * * * *